(12) United States Patent
Holcomb et al.

(10) Patent No.: US 6,753,145 B2
(45) Date of Patent: Jun. 22, 2004

(54) BUFFER COMPOSITION AND METHOD FOR HYBRIDIZATION OF MICROARRAYS ON ADSORBED POLYMER SILICEOUS SURFACES

(75) Inventors: Nelson R. Holcomb, San Jose, CA (US); Patrick J. Collins, San Francisco, CA (US); Karen W. Shannon, Los Gatos, CA (US); Steven M. Lefkowitz, Millbrae, CA (US)

(73) Assignee: Agilent Technologies, Inc., Palo Alto, CA (US)

( * ) Notice: Subject to any disclaimer, the term of this patent is extended or adjusted under 35 U.S.C. 154(b) by 0 days.

(21) Appl. No.: 09/900,084

(22) Filed: Jul. 5, 2001

(65) Prior Publication Data

US 2003/0013092 A1 Jan. 16, 2003

(51) Int. Cl.⁷ .......................... C12Q 1/68; C12N 15/00; C12N 15/63; C12N 1/20; C07H 21/04
(52) U.S. Cl. .................. 435/6; 435/320.1; 435/252.8; 435/174; 435/183; 382/129; 382/133; 382/153; 382/173; 382/286; 382/291; 702/19; 702/22; 935/10; 935/24; 935/72; 536/22.1
(58) Field of Search .................. 435/6, 91.1, 91.2, 435/287.2, 287.3, 7.1; 536/24.3, 23.1, 24.1; 935/6; 436/518, 501, 514, 807

(56) References Cited

U.S. PATENT DOCUMENTS

| | | | |
|---|---|---|---|
| 5,800,984 A | | 9/1998 | Vary |
| 5,807,522 A | | 9/1998 | Brown et al. |
| 6,177,248 B1 | | 1/2001 | Oliner et al. |
| 6,203,989 B1 | * | 3/2001 | Goldberg et al. .............. 435/6 |
| 6,252,059 B1 | * | 6/2001 | McDonough et al. .... 536/24.32 |
| 6,262,216 B1 | | 7/2001 | McGall |
| 6,316,608 B1 | * | 11/2001 | Reynolds et al. .......... 536/22.1 |
| 6,322,989 B1 | * | 11/2001 | Cohen ........................ 435/7.1 |
| 6,451,260 B1 | * | 9/2002 | Dusterhoft ................. 422/68.1 |
| 6,495,327 B2 | * | 12/2002 | Milliman ........................ 435/6 |

FOREIGN PATENT DOCUMENTS

| | | |
|---|---|---|
| EP | 1 186 671 | 3/2002 |
| EP | 1 262 566 | 12/2002 |
| WO | WO 98/13527 | 4/1998 |
| WO | WO 01/42501 | 6/2001 |
| WO | WO 01/42512 | 6/2001 |

OTHER PUBLICATIONS

Duca, K.A. et al., "Nuclear clustering in myotubes: a proposed role in acetylcholine receptor mRNA expression", Biochimica et Biophysica Acta, vol. 1401, 1998, pp. 1–20.

Dignam, J.D. et al., "Accurate transcription initiation by RNA polymerase II in a soluble extract from isolated mammalian nuclei", Nucleic Acids Research, vol. 11, No. 5, 1983, pp. 1475–1489.

Cataldo, L. M. et al., "Rat NAP1: cDNA cloning and upregulation by MP1 ligand", GENE, vol. 226, 1999, pp. 355–364.

Nishida, K. et al., "Association of the proto–oncogene product Dbl with G protein Beta Gamma subunits", FEBS Letters, vol. 459, 1999, 186–190.

Hughes, T.R. et al., "Expression profiling using microarrays fabricated by an ink–jet oligonucleotide synthesizer", Nature Biotechnology, vol. 19, 2001, pp. 342–347.

Marton, M.J. et al., "Drug target validation and identification of secondary drug target effects using DNA microarrays", Nature Medicine, vol. 4, No. 11, 1998, pp. 1293–1301.

Schena, M. et al., "Quantitative Monitoring of Gene Expression Patterns with a Complementary DNA Microarray", SCIENCE, vol. 270, 1995, pp. 467–470.

Zammatteo, N. et al., "Comparison between Different Strategies of Covalent Attachment of DNA to Glass Surfaces to Build DNA Microarrays", Analytical Biochemistry, vol 280, 2000, pp. 143–150.

Communication from European Patent Office dated Mar. 3, 2003, EP Search Report dated Feb. 20, 2003.

* cited by examiner

Primary Examiner—Jeffrey Fredman
Assistant Examiner—Arun Chakrabarti

(57) ABSTRACT

A buffer composition, method and kit for hybridizing microarrays of nucleic acids bound to an adsorbed polymer surface of a siliceous substrate provide an envelope of conditions to hybridize nucleic acid targets, while preserving the intactness of the adsorbed polymer surface of the array. The buffer composition comprises a non-chelating buffering agent, a pH within a range of pH 6.4 and 7.5, a monovalent cation having a monovalent cation concentration that ranges from about 0.01 M to about 2.0 M, and optionally relatively lower concentrations of a chelating agent and an ionic surfactant. The total cation concentration of the buffer composition ranges from about 0.02 M to about 2.0 M. The method comprises incubating the targets with the microarray in the buffer composition at a temperature between about 55° C. and 70° C.

20 Claims, No Drawings

BUFFER COMPOSITION AND METHOD FOR HYBRIDIZATION OF MICROARRAYS ON ADSORBED POLYMER SILICEOUS SURFACES

CROSS-REFERENCE TO RELATED APPLICATION

This application is related to a pending patent application entitled "Method For Hybridization of Arrays On Siliceous Surfaces", Inventors Karen W. Shannon and Steven M. Lefkowitz, Ser. No. 09/655,482, filed Sep. 5, 2000 and has the same assignee as this application.

TECHNICAL FIELD

This invention relates to biological assays. In particular, the invention is directed to materials and methods of hybridizing microarrays of nucleic acid molecules for analytical, therapeutic and diagnostic purposes.

BACKGROUND ART

Microarrays of DNA or RNA polynucleotides or oligonucleotides are state-of-the-art biological tools used in the investigation and evaluation of genes for analytical, diagnostic, and therapeutic purposes. Microarrays typically comprise a plurality of oligomers, synthesized or deposited on a glass support or substrate in an array pattern. The support-bound oligomers are called "probes" and function to bind or hybridize with a sample of DNA or RNA material under test, called a "target" in hybridization experiments. However, some investigators bind the target sample under test to the microarray substrate and put the oligomer probes in solution for hybridization. Moreover, some investigators use the reverse definition, referring to the surface-bound oligonucleotides as targets and the solution sample of nucleic acids as probes. Either of the "targets" or "probes" may be the one that is to be evaluated by the other (thus, either one could be an unknown mixture of polynucleotides to be evaluated by binding with the other). All of these iterations are within the scope of this discussion herein. In use, the microarray surface is contacted with one or more targets under conditions that promote specific, high-affinity binding of the target to one or more of the probes. The targets are typically labeled with an optically detectable label, such as a fluorescent tag, so that the hybridized targets and probes are detectable with scanning equipment. DNA array technology offers the potential of using a multitude (hundreds of thousands) of different oligonucleotides to analyze changing mRNA populations.

There are numerous types of substrates used in hybridization assays. Common substrates or supports used for microarray assays are siliceous substrates, such as glass. The surface of the substrates are typically treated or derivatized to facilitate binding of the probes to the substrate. For in situ synthesis of probes, the first monomers of the oligomer probe sequences are attached to the substrate surface that is derivatized with a silane or other compounds known in the art to facilitate the bonding of the first monomers. Subsequent monomers are added directly to the monomers of the growing oligomer chain. For deposition of presynthesized or whole probes, such as cDNA probes, the probe is attached to a polymer adsorbed or coated on the surface of the substrate to facilitate bonding. The adsorbed polymer is coated and dried on the substrate surface. The substrate surface derivatizations enable and facilitate the attachment of nucleic acids to the surface of microarray substrates for the manufacture of the microarrays. Surface treatments or derivatization techniques, including those mentioned above, are well known in the art.

Microarrays of oligomer probes, such as oligonucleotides or polynucleotides, are hybridized using conventional methods and hybridization solutions. J. Sambrook, E. F. Fritsch, T. Maniatis, *Molecular Cloning: A Laboratory Manual*, Cold Spring Harbor Laboratory Press, Cold Spring Harbor, Ed. $2^{nd}$, 1989, vol. 1–3, incorporated herein by reference, describe the considerations and conditions for hybridization of oligonucleotide probes. Probe length, hybridization temperature, as well as other factors that are well known in the art affect hybridization conditions. Typically, hybridizations using synthetic oligomers are usually carried out under conditions that are 5–10° C. below the calculated melting temperature $T_m$ of a perfect hybrid to minimize mismatched or non-Watson/Crick base pairing between the probe and target, and maximize the rate at which Watson/Crick base pairs form. Other factors influencing the rate of hybrid formation include the salt concentration, the presence of surfactants, solvents or co-solvents, the concentration of nucleic acid in solution, the length of hybridization, and the degree and method of agitation.

The hybridization solution typically comprises a salt (monovalent cation), either SSPE or SSC buffer that provides buffering capacity between pH 6.8–8.5 (more typically between pH 7.0–7.5), a divalent cation chelating agent (e.g. ethylenediaminetetraacetic acid, EDTA), and agents for blocking non-specific binding of targets to the array surface (surfactants, proteins and/or carrier DNA from an organism unrelated to the experiment at hand). More specifically, a typical hybridization solution contains 6×SSPE (0.9 M NaCl, 60 mM sodium phosphate (pH 7.4); 6 mM EDTA); or 6×SSC (0.9 M NaCl, 90 mM sodium citrate (pH 7.0)), 0.5% w/v sodium dodecyl sulfate (SDS); 100 μg/ml denatured, fragmented salmon sperm DNA; and 0.1% nonfat dried milk.

The microarray is hybridized for a period of time ranging from about 2 hours to about 2 days, depending on the make-up of the probes (i.e., probe length and diversity of probe composition) and the complexity of the target, for example, at a controlled temperature, which typically ranges from 20° C. to 70° C., depending on the melting temperature $T_m$, as discussed above. Low temperature hybridizations are performed at about 20° C. to about 50° C. (typically about 37–45° C.). High temperature hybridizations are performed at or around 55° C. to about 70° C. (typically 60° C. to 65° C.). However, for most nucleic acid microarrays, high temperature hybridizations are preferred in the art since the higher temperature maximizes the rate of Watson/Crick base pairing of nucleotides, while low temperature hybridizations typically maximize Watson/Crick base pairings by use of a co-solvent to lower the $T_m$. The typical time period for hybridization of a microarray is overnight or longer (i.e., anywhere from 8 hours to 24 hours) so as to hybridize the target. The array is then washed and dried and optically scanned to measure the degree of hybridization using conventional methods and equipment that are well known in the art.

A problem in the DNA microarray hybridization art is sporadic poor hybridization assay performance characterized by low-intensity or missing features on the microarray substrate, high backgrounds, and visually "blotchy" substrates. For microarrays containing DNA on adsorbed polymer substrate surfaces, this problem has been observed using conventional hybridization conditions, such as using a solution comprising 20×SSC (3.0 M NaCl, 300 mM Sodium Citrate (pH 7.0), 10% SDS) at high hybridization temperature of about 65° C. and within conventional hybridization times of about 6 hrs. to about 24 hours.

Thus, it would be advantageous to have materials, conditions and methods of hybridizing arrays of oligomers on siliceous substrates that have been treated or coated with a surface adsorbed polymer in biological assays at the preferred higher hybridization temperature range and longer hybridization times without affecting the hybridization assay performance.

SUMMARY OF THE INVENTION

The present invention provides a buffer composition and method for hybridizing nucleic acid microarrays with other nucleic acid materials used in high throughput analytical, therapeutic, and diagnostic applications. The method uses an envelope of hybridization conditions for performing assays at high hybridization temperatures for long periods of time. The hybridization conditions of the method advantageously are compatible with siliceous substrates having adsorbed polymer surfaces. The buffer composition and method of the present invention work particularly well on adsorbed polycationic polymer coated siliceous surfaces. The envelope of conditions addresses solution pH and buffer type, salt composition, surfactant composition, temperature and time. The present invention allows sensitive, selective detection of nucleic acid targets, while preserving the intactness of the adsorbed polymer siliceous surface. The buffer composition and method of the invention overcome the problems found in the art by reducing delamination of the surface polymer and reducing residues when performing assays on adsorbed polymer siliceous substrate surfaces at high hybridization temperatures between about 55° C. and 70° C. for time periods used to hybridize a target material. The buffer composition and method of the present invention provide optimized hybridization assay performance by maintaining the integrity of the adsorbed polymer surface of the siliceous substrates.

In one aspect of the invention, a buffer composition for hybridization assays of arrays of oligonucleotides bound to an adsorbed polymer substrate surface with another nucleic acid material is provided. The buffer composition comprises a pH in a range of pH 6.4 to 7.5, a monovalent cation having a monovalent cation concentration ranging from about 0.01 M to 2.0 M, and a non-chelating buffering agent that maintains the pH within the pH range. The buffer composition may optionally further comprise relatively lower concentrations of an ionic surfactant and/or a chelating agent. The buffer composition has a total cation concentration ranging from about 0.02 M to about 2.0 M, accounting for all components in the buffer solution. In one embodiment, the buffer composition further comprises nucleic acids in solution and is used in a hybridization assay of a nucleic acid material under test that is attached to an adsorbed polymer surface of a siliceous substrate.

In another aspect of the invention, a method of hybridizing a microarray of oligonucleotides on an adsorbed polymer surface of a siliceous substrate with another nucleic acid material is provided. The method of hybridizing comprises the step of incubating the nucleic acid material with the microarray of oligonucleotides on the adsorbed polymer surface in a hybridization solution at a hybridization temperature ranging from about 55° C. to about 70° C. so as to hybridize the nucleic acid material, wherein the hybridization solution comprises a buffer composition that comprises a pH within a range of pH 6.4 and 7.5, a non-chelating buffering agent, and a monovalent cation in a monovalent cation concentration ranging from about 0.01 M to about 2.0 M. The buffer composition may optionally further comprise relatively lower concentrations of a chelating agent and/or an ionic surfactant.

In still another aspect of the invention, a buffer kit for performing hybridization assays on siliceous substrates having an adsorbed polymer on the substrate surface is provided. In one embodiment, the kit comprises the buffer composition of the present invention that comprises a non-chelating buffering agent, a pH within a range of pH 6.4 and 7.5 and a total cation concentration ranging from about 0.02 M to about 2.0 M. In another embodiment, the kit comprises a components list for the buffer composition of the present invention. The components list comprises the components of the buffer composition of the present invention described above. Optional instructions may be included in the kits. The optional instructions comprise the method of the present invention described above, or instructions for using the buffer composition in a hybridization assay of a nucleic acid material with a siliceous substrate that has an adsorbed polymer surface for attaching to nucleic acids. In still another embodiment, the kit may further a nucleic acid sample for use as a hybridization assay control. Still further, the buffer composition in the kit may further comprise nucleic acids in solution, or the kit may further comprise a microarray of nucleic acids attached to an adsorbed polymer surface of a siliceous array substrate for use with a nucleic acid material in a hybridization assay.

The buffer composition, method and kit of the present invention overcome the problems in the art by reducing degradation of the adsorbed polymer surface of the microarray substrate and any further etching of the substrate, both of which impact the hybridization results between nucleic acid probes and target materials at high temperatures. Further, the present invention does not affect the signal intensities of the fluorescent labeling system used in conventional hybridization assays. The hybridization conditions and methods of the present invention are particularly useful in DNA or RNA microarray assays performed at high temperatures, i.e., above about 55° C., and for longer hybridization times, i.e., equal to or greater than about 6 hours, where conventional buffer compositions, including but not limited to SSC and SSPE react with the conventional adsorbed polymer surface of siliceous substrates, and affect hybridization results.

BRIEF DESCRIPTION OF THE DRAWINGS

No drawings are included with this application.

MODES FOR CARRYING OUT THE INVENTION

The various features and advantages of the present invention may be more readily understood with reference to the following Definitions, Detailed Description and Example.

DEFINITIONS

The following terms are intended to have the following general meanings as they are used herein:

Nucleic acid—a high molecular weight material that is a polynucleotide or an oligonucleotide of DNA or RNA.

Polynucleotide—a compound or composition that is a polymeric nucleotide or nucleic acid polymer. The polynucleotide may be a natural compound or a synthetic compound. In the context of an assay, the polynucleotide can have from about 20 to 5,000,000 or more nucleotides. The larger polynucleotides are generally found in the natural state. In an isolated state the polynucleotide can have about 30 to 50,000 or more nucleotides, usually about 100 to 20,000 nucleotides, more frequently 500 to 10,000 nucleotides. It is thus obvious that isolation of a polynucleotide from the natural state often results in fragmentation. The polynucleotides include nucleic acids, and fragments thereof, from any source in purified or unpurified form including DNA, double-stranded or single-stranded (dsDNA and ssDNA), and RNA, including t-RNA, m-RNA, r-RNA, mitochondrial DNA and RNA, chloroplast DNA and RNA, complementary DNA (cDNA) (a single stranded DNA that is complementary to an RNA and synthesized from the RNA in vitro using reverse transcriptase), DNA/RNA hybrids, or mixtures thereof, genes, chromosomes, plasmids, the genomes of biological materials such as microorganisms, e.g. bacteria, yeasts, viruses, viroids, molds, fungi, plants, animals, humans, and the like. The polynucleotide can be only a minor fraction of a complex mixture such as a biological sample. Also included are genes, such as hemoglobin gene for sickle-cell anemia, cystic fibrosis gene, oncogenes, and the like.

Polynucleotides include analogs of naturally occurring polynucleotides in which one or more nucleotides are modified over naturally occurring nucleotides. Polynucleotides then, include compounds produced synthetically (for example, PNA as described in U.S. Pat. No. 5,948,902 and the references cited therein, all of which are incorporated herein by reference), which can hybridize in a sequence specific manner analogous to that of naturally occurring complementary polynucleotides.

The polynucleotide can be obtained from various biological materials by procedures well known in the art. The polynucleotide, where appropriate, may be cleaved to obtain a fragment that contains a target nucleotide sequence, for example, by shearing or by treatment with a restriction endonuclease or other site-specific chemical cleavage method.

For purposes of this invention, the polynucleotide, or a cleaved fragment obtained from the polynucleotide, will usually be at least partially denatured or single-stranded or treated to render it denatured or single-stranded. Such treatments are well known in the art and include, for instance, heat or alkali treatment, or enzymatic digestion of one strand. For example, double stranded DNA (dsDNA) can be heated at 90–100° C. for a period of about 1 to 10 minutes to produce denatured material, while RNA produced via transcription from a dsDNA template is already single-stranded.

Oligonucleotide—a polynucleotide, usually single-stranded, usually a synthetic polynucleotide but may be a naturally occurring polynucleotide. The oligonucleotide(s) are usually comprised of a sequence of at least 5 nucleotides, usually, 10 to 100 nucleotides, preferably, 20 to 60 nucleotides, more preferably, 20 to 35 nucleotides, and desirably about 25 nucleotides in length.

Various techniques can be employed for preparing an oligonucleotide. Such oligonucleotides can be obtained by biological synthesis or by chemical synthesis. For short sequences (up to about 100 nucleotides), chemical synthesis will frequently be more economical as compared to the biological synthesis. In addition to economy, chemical synthesis provides a convenient way of incorporating low molecular weight compounds and/or modified bases during specific synthesis steps. Furthermore, chemical synthesis is very flexible in the choice of length and region of target polynucleotides binding sequence. The oligonucleotide can be synthesized by standard methods such as those used in commercial automated nucleic acid synthesizers. Chemical synthesis of DNA on a suitably modified glass or resin can result in DNA covalently attached to the surface. This may offer advantages in washing and sample handling. For longer sequences standard replication methods employed in molecular biology can be used such as the use of M13 for single-stranded DNA as described in J. Messing (1983) *Methods Enzymol.* 101:20–78.

Other methods of oligonucleotide synthesis include phosphotriester and phosphodiester methods (Narang, et al., (1979) *Meth. Enzymol.* 68:90) and synthesis on a support (Beaucage, et al. (1981) *Tetrahedron Letters* 22:1859–1862) as well as phosphoramidate techniques (Caruthers, M. H., et al., "Methods in Enzymology," Vol. 154, pp. 287–314 (1988) and others described in "Synthesis and Applications of DNA and RNA," S. A. Narang, editor, Academic Press, New York, 1987, and the references contained therein. The chemical synthesis via a photolithographic method of spatially addressable arrays of oligonucleotides bound to glass surfaces is described by A. C. Pease, et al., *Proc. Nat. Aca. Sci. USA* (1994) 91:5022–5026. Unless otherwise noted herein, the terms nucleic acid, oligonucleotide and polynucleotide are intended to be used interchangeably.

Nucleotide—the monomeric unit of nucleic acid polymers, i.e., DNA and RNA, whether obtained from a natural source or produced synthetically, which comprises a nitrogenous heterocyclic base, which is a derivative of either a purine or pyrimidine, a pentose sugar, and a phosphate (or phosphoric acid). When the phosphate is removed, the monomeric unit that remains is a "nucleoside". Thus a nucleotide is a 5'-phosphate of the corresponding nucleoside. When the nitrogenous base is removed from the nucleotide, the monomeric unit that remains is a "phosphodiester". For the purposes of the invention, "nucleotide" includes its corresponding nucleoside and phosphodiester, and "oligonucleotide" includes its corresponding oligonucleoside and oligophosphodiester, unless indicated otherwise. The term "nucleotide" includes "modified nucleotide" that contains a modified base, sugar or phosphate group. The modified nucleotide can be produced by a chemical modification of a nucleotide either as part of the nucleic acid polymer or prior to the incorporation of the modified nucleotide into the nucleic acid polymer. For example, the methods mentioned above for the synthesis of an oligonucleotide may be employed. In another approach, a modified nucleotide can be produced by incorporating a modified nucleoside triphosphate into the polymer chain during an amplification reaction. Examples of modified nucleotides, by way of illustration and not limitation, include dideoxynucleotides, derivatives or analogs that are biotinylated, amine modified, alkylated, fluorophore-labeled, and the like and also include phosphorothioate, phosphite, ring atom modified derivatives, and so forth.

Target material or target—a sequence of nucleotides to be identified, usually existing within a portion or all of a polynucleotide, usually a polynucleotide analyte. The identity of the target nucleotide sequence generally is known to a extent sufficient to allow preparation of various probe sequences hybridizable with the target material.

The target material usually contains from about 30 to 5,000 or more nucleotides, preferably 50 to 1,000 nucleotides. The target material is generally a fraction of a larger molecule or it may be substantially the entire molecule such as a polynucleotide as described above. The minimum number of nucleotides in the target material is selected to assure that the presence of a target polynucleotide in a sample is a specific indicator of the presence of polynucleotide in a sample. The maximum number of nucleotides in the target material is normally governed by several factors: the length of the polynucleotide from which it is derived, the tendency of such polynucleotide to be broken by shearing or other processes during isolation, the efficiency of any procedures required to prepare the sample for analysis (e.g. transcription of a DNA template into RNA) and the efficiency of detection and/or amplification of the target nucleotide sequence, where appropriate.

Nucleic acid probe—an oligonucleotide or polynucleotide employed to bind to a portion of a polynucleotide such as another oligonucleotide or a target material. The design and preparation of the nucleic acid probes are generally dependent upon the sensitivity and specificity required, the sequence of the target material and, in certain cases, the biological significance of certain portions of the target material.

Hybridization (hybridizing) and binding—in the context of nucleotide sequences these terms are used interchangeably herein. The ability of two nucleotide sequences to hybridize with each other is based on the degree of complementarity of the two nucleotide sequences, which in turn is based on the fraction of matched complementary nucleotide pairs. The more nucleotides in a given sequence that are complementary to another sequence, the more stringent the conditions can be for hybridization and the more specific will be the binding of the two sequences. Increased stringency is achieved by elevating the temperature, increasing the ratio of co-solvents, lowering the salt concentration, and the like. For the purposes of the invention, hybridization of complementary Watson/Crick base pairs of probes on the microarray and of the target material is preferred, but non Watson/Crick base pairing during hybridization may also occur.

Conventional hybridization solutions and processes for hybridization are described in J. Sambrook, E. F. Fritsch, T. Maniatis, *Molecular Cloning: A Laboratory Manual*, Cold Spring Harbor Laboratory Press, Cold Spring Harbor, Ed. $2^{nd}$, 1989, vol. 1–3, incorporated herein by reference. Conditions for hybridization typically include (1) high ionic strength solution, (2) at a controlled temperature, and (3) in the presence of carrier DNA and surfactants and chelators of divalent cations, all of which are well known in the art.

Complementary—Two sequences are complementary when the sequence of one can bind to the sequence of the other in an anti-parallel sense wherein the 3'-end of each sequence binds to the 5'-end of the other sequence and each A, T(U), G, and C of one sequence is then aligned with a T(U), A, C, and G, respectively, of the other sequence, to form Watson/Crick base pairs. RNA sequences can also include complementary G=U or U=G base pairs. Non-standard or non Watson/Crick base pairing is also possible with nucleotide complements, for instance, the sequences may be parallel to each other and complementary A=C or G=U base pairs in RNA sequences or complementary G=T or A=C base pairs in DNA sequences may occur, although are not preferred.

Substrate or surface—a porous or non-porous water insoluble support material. The surface can have any one of a number of shapes, such as strip, plate, disk, rod, particle, including bead, and the like. The substrate can be hydrophobic or hydrophilic or capable of being rendered hydrophobic or hydrophilic and includes inorganic powders such as silica, magnesium sulfate, and alumina; natural polymeric materials, particularly cellulosic materials and materials derived from cellulose, such as fiber-containing papers, e.g., filter paper, chromatographic paper, etc.; synthetic or modified naturally occurring polymers, such as nitrocellulose, cellulose acetate, poly (vinyl chloride), polyacrylamide, cross linked dextran, agarose, polyacrylate, polyethylene, polypropylene, poly (4-methylbutene), polystyrene, polymethacrylate, poly(ethylene terephthalate), nylon, poly (vinyl butyrate), etc.; either used by themselves or in conjunction with other materials; glass available as Bioglass, for example, quartz, ceramics, metals, and the like. Natural or synthetic assemblies such as liposomes, phospholipid vesicles, and cells can also be employed.

Common substrates used for microarrays in accordance with the invention are surface-derivatized glass or silica, or polymer membrane surfaces, as described in Z. Guo et al. (cited above) and U. Maskos, E. M. Southern, *Nucleic Acids Res* 20, 1679–84 (1992) and E. M. Southern et al., *Nucleic Acids Res* 22, 1368–73 (1994), both incorporated herein by reference. In modifying siliceous or metal oxide surfaces, one technique that has been used is derivatization with bifunctional silanes, i.e., silanes having a first functional group enabling covalent binding to the surface (often an Si-halogen or Si-alkoxy group, as in $SiCl_3$ or $-Si(OCH_3)_3$, respectively) and a second functional group that can impart the desired chemical and/or physical modifications to the surface to covalently or non-covalently attach ligands and/or the polymers or monomers for the biological probe array. See, for example, U.S. Pat. No. 5,624,711 to Sundberg, U.S. Pat. No. 5,266,222 to Willis and U.S. Pat. No. 5,137,765 to Farnsworth, each incorporated herein by reference.

Adsorbed polymer surfaces are used on siliceous substrates for attaching nucleic acids, for example cDNA, to the substrate surface. Substrates can be purchased with a polymer coating, or substrates can be coated with a solution containing a polymer and dried according to well-known procedures. For a typical protocol for substrate coating see website http://cmgm.stanford.edu/pbrown/protocols/1_slides.html.

Immobilization of oligonucleotides on a substrate or surface may be accomplished by well-known techniques, commonly available in the literature. See, for example, A. C. Pease, et al., *Proc. Nat. Acad. Sci. USA*, 91:5022–5026 (1994); Z. Guo, R. A. Guilfoyle, A. J. Thiel, R. Wang, L. M. Smith, *Nucleic Acids Res* 22, 5456–65 (1994); and M. Schena, D. Shalon, R. W. Davis, P. O. Brown, *Science*, 270, 467–70 (1995), each incorporated herein by reference.

Siliceous substrate—Any material largely comprised of silicon dioxide, including but not limited to, glass and quartz.

Feature—a feature is a location on a microarray substrate characterized by having either nucleic acid probes or targets bonded to the substrate. The location of a feature is addressable, typically by a row and column location. A microarray comprises a plurality of sets of features.

DETAILED DESCRIPTION OF THE INVENTION

Although the inventors do not want to be held to any particular theory for the cause of the problem in the hybridization assay art, the inventors believe that the conventional hybridization solutions and conditions at the preferred high temperatures above 50° C. for 6 hours or more were degrading the surface adsorbed polymer siliceous substrate. The co-pending application Ser. No. 09/655,482, which is incorporated by reference herein in its entirety, addressed degradation of surface-derivatized siliceous substrates, and possibly further dissolution of the siliceous substrate itself with time. In particular, the co-pending application addressed degradation of silylated-siliceous substrates used for in situ synthesis of oligomers on microarray substrates. Characteristics, such as the low-intensity or missing features on the assay substrate, high backgrounds, and/or visually "blotchy" substrates after hybridization assays appeared consistent with substrate surface dissolution.

The present invention addresses siliceous substrates coated with an adsorbed polymer that are typically used with presynthesized oligonucleotide or cDNA arrays. The adsorbed polymer surface on the siliceous substrate is a conventional polymer coating used to facilitate immobilization of the nucleic acids to the siliceous substrate surface. All adsorbed polymers that are or may be used to facilitate bonding nucleic acids or other biological materials to a microarray substrate surface are within the scope of the invention. A polycationic polymer coating is one type of an adsorbed polymer surface with which the present invention works particularly well.

The co-pending application Ser. No. 09/655,482 disclosed that the buffer and the pH of the hybridization solution played an important role in the quality of hybridization assay results and surface uniformity. It appeared that some of the conventional hybridization buffers at conventional solution pH were not compatible with hybridization assays at high temperature and repeatedly produced poor hybridization assay results, such as hybridized features having low-intensity or missing features from the substrate surface. The present invention addresses both the surface dissolution problem and assay performance for DNA microarrays on siliceous substrates with an adsorbed polymer surface. The method of the present invention provides optimized hybridization assay performance and maintains the integrity of the adsorbed polymer surface of the siliceous substrates.

Substrates or supports used in biological assays in analytical, therapeutic and diagnostic applications using nucleic acid microarrays are as defined above. Typical substrates for microarray applications are soda lime glass, pure silica, heat resistant glasses, quartz or other materials that are typically coated with a polymer to improve bonding of nucleic acids to the surface, as is well known in the art. Advantageously, the method of the present invention reduces delamination of the surface adsorbed polymer, and reduces degradation of the siliceous substrate and of hybridization assay performance thereon at high hybridization temperatures ranging from 55° C. to 70° C. relative to the conventional sodium citrate and phosphate buffers.

In general, hybridizations conventionally can take anywhere from less than about 2 hours to more than 48 hours to be completed at hybridization temperatures ranging from about 20° C. to about 70° C. However, the adsorbed polymer substrate surface degradation problem in the art was more prevalent when conventional citrate buffers and higher temperatures and/or longer hybridization (incubation) times were used. Higher temperature hybridizations at about 55° C. to about 70° C. are known in the art to advantageously maximize the rate of Watson/Crick base pairing than lower temperature hybridizations at about 20° C. to about 50° C., and therefore, higher temperature hybridizations are preferred for the purposes of the invention.

Moreover, hybridization "completion" is dependent on the user and the target nucleic acid material to be hybridized. The time for hybridization is not intended to limit the scope of the invention, but instead, the hybridization time is intended to emphasis the benefit of the invention. Hybridization could comprise anywhere from 1% to 100% of the substrate-bound nucleic acids on at least one feature of the microarray being hybridized with the target material, for example. The hybridization time periods to achieve completion within the 1% to 100% range will vary greatly. The hybridization time periods at the higher temperatures usually are about 8 hours to about 24 hours (or longer) typically, to achieve optimum results or throughput, when the nucleotide make-up of the mixture of probes is diverse and/or the target population is complex. However, the problem of substrate dissolution in the art was visible in hybridizations as early as about 6 hours during high temperature hybridizations.

In accordance with one aspect of the invention, a buffer composition for use in hybridization assays of arrays of oligonucleotides bound to an adsorbed polymer surface of a siliceous substrate is provided. The buffer composition comprises a non-chelating buffering agent having a buffering capacity between pH 6.4 and 5.5. The buffer solution further comprises a monovalent cation in a monovalent cation concentration ranging from about 0.01 M to about 2.0 M. The pH of the buffer solution is maintained at a pH within a range of pH 6.4 to 7.5.

The buffer composition optionally further comprises relatively lower concentrations of an ionic surfactant and/or a chelating agent. By 'relatively lower concentrations' it is meant that the concentration of each of the ionic surfactant and the chelating agent is much less than the concentration of the monovalent cation. The buffer composition has a total cation concentration (accounting for all components in the buffer composition) that ranges from about 0.02 M to about 2.0 M. Preferably the total cation concentration ranges from about 0.1 M to 2.0 M and more preferably, is about 750 mM. The pH of the buffer composition preferably ranges from pH 6.4 to 7.0. More preferably, the pH of the buffer composition ranges from pH 6.6 to 6.8, wherein a pH of 6.7 is considered optimal for the buffer composition of the present invention.

For the purposes of the invention, 'non-chelating' with respect to the buffering agent generally means that the buffering agent does not contain a carboxylic acid functionality and further, that the buffering agent is not a phosphate-containing buffering agent. Chelating action has been found to reduce the stability of the adsorbed polymer surface of the microarray, and is the largest determinant of the stability of the adsorbed polymer surface. By 'buffering capacity' it is meant that the buffering agent has the ability to buffer or maintain a constant pH or a pH range during a hybridization assay at the hybridization temperature.

The present buffer composition comprises a non-chelating buffering agent selected from a group consisting of alkyl sulfonic acid-containing and alkyl amine-containing buffering agents, having a buffering capacity between pH 6.4 and 7.5 (i.e., can buffer within the range of the pH for the invention). Non-chelating buffering agents (i.e., those that do not comprise a carboxylic acid functionality or a phosphate group) that have a buffering capacity that includes a pH in the pH range of 6.4 to 7.5 and that are soluble at the concentration of interest are within the scope of the invention. Table 1 provides a list of some non-chelating buffering agents applicable to the invention. This list is illustrative only and not intended to limit the scope of the present buffer composition. Non-chelating buffering agents that have a useful pH range within or close to the pH range of interest will provide a high confidence level that the buffering agents will maintain the pH within the appropriate range of pH 6.4–7.5 during the course of a hybridization assay. The buffer composition of the present invention preferably uses as the buffering agent 2-[N-morpholino]ethanesulfonic acid (MES), having a reported pKa at about 25° C. of 6.15 and a useful pH range of 5.5 to 6.7 (Daniel C. Harris, *Quantitative Chemical Analysis*, 3$^{rd}$ Ed., W H Freeman and Co., New York, 1991). Other alkyl sulfonic acid- or alkyl amine-containing buffering agents useful for the present buffer composition, such as 3-(N-Morpholine)propanesulfonic acid (MOPS), Piperazine-NN'-bis(2-ethansulfonic acid (PIPES), Tris(hydroxymethyl)aminomethane hydrochloride (TRIS-HCl), Hydroxyethylpiperazine-N'-2-ethanesulfonic acid (HEPES), and N-Tris(hydroxymethyl)methylglycine (TRICINE), are listed in Table 1 below. For a discussion on buffering agents, buffering capacity, useful pH range and standard buffer concentrations for hybridization assays, see J. Sambrook, E. F. Fritsch, T. Maniatis, *Molecular Cloning: A Laboratory Manual*, Cold Spring Harbor Laboratory Press, Cold Spring Harbor, Ed. 2$^{nd}$, 1989, vol. 1–3, incorporated herein by reference.

The buffering agent has many functions, including but not limited to maintaining the pH and acting as a counter ion to the phosphate backbone of the DNA to keep the DNA in solution during an assay. For the invention, the non-chelating buffering agent also helps to keep the adsorbed polymer surface stable. The buffering agent typically is provided in a hybridization solution at a concentration that is much greater than the typical concentration of the DNA sample being assayed. For example, typically the buffering agent concentration is provided in the molar (M) range, while a typical DNA sample concentration is in the picomolar (PM) range. Therefore, even though the 'Useful pH range' of some buffering agents listed in Table 1 are outside of the pH range of interest of pH 6.4 to 7.5, these buffering agents can maintain the pH of a hybridization assay in accordance with the invention within the pH range of interest and can keep the adsorbed polymer surface stable.

TABLE 1

Non-chelating Buffering Agents

| Buffering Agent | pKa at ~25° C. | Useful pH range |
| --- | --- | --- |
| MES | 6.15 | 5.5–6.7 |
| MOPS | 7.20 | 6.6–7.8 |
| Imidazole hydrochloride | 6.99 | 6.4–7.6 |
| PIPES | 6.80 | 6.2–7.4 |
| TRIS-HCl | 8.08 | 7.8–8.3 |
| HEPES | 7.56 | 7.0–7.8 |
| TRICINE | 8.1 | 7.7–8.4 |

The conventional saline sodium citrate (SSC) buffer severely destabilizes the adsorbed polymer surface under normal high temperature hybridization conditions and is not recommended in accordance with the invention. Conventional SSC buffers have pka's of 3.13 ($pK_1$), 4.76 ($pK_2$), and 6.40 ($pK_3$) at 25° C. and a useful pH range of about 3 to about 7. Although the inventors do not want to be held to any particular theory for the destabilizing effect of the conventional SSC buffers, the inventors believe that the destabilization effects are attributed to the presence of carboxylate functional groups on the citrate$^{-3}$ ion near the pH of interest. The adsorbed polymer surface, especially a polycationic polymer surface, seems to be destabilized by carboxylate functional groups and also phosphate groups. Therefore, a buffering agent with carboxylate or phosphate functional groups is not recommended even if its useful pH range is at or close to the pH range of interest.

In the buffer composition of the present invention, the monovalent cation is provided by a salt selected from one or more of NaCl, LiCl or KCl, and preferably is LiCl. An adsorbed polymer surface, such as a polycationic polymer surface, is stabilized by increasing cationic strength. The concentration of the monovalent cation in the buffer composition of the present invention ranges from about 0.01 M to 2.0 M, and preferably, the lower limit is much greater than about 0.01 M. Below a total cation concentration of about 0.02 M, the adsorbed polymer surface is destabilized and easily destroyed. Above about 2.0 M of total cation concentration, it is believed that there is interference with the hybridization assay. Preferably, the concentration of monovalent cation, and consequently, the total cation concentration are within the range of about 0.10 M to about 2.0 M. More preferably, the total cation concentration in the buffer composition is about 750 mM and the buffer composition comprises Li-MES as the buffering agent. By 'much greater' it is meant at least about 10 to about 200 times greater or more. By 'much less' it is meant at least about 5 to about 10 times less (or possibly>10 times less). By 'about' it is meant within the range of ±5% to 10%.

In addition to the non-chelating buffering agent and the monovalent cation, the buffer composition optionally may further comprise relatively lower concentrations of a chelating agent and/or an ionic surfactant. As mentioned above 'relatively lower concentrations' are relative to the concentration of the monovalent cation (or the total cation concentration). Typically, the chelating agent is used to sequester divalent cations that stabilize nucleic acid tertiary structures. However, as mentioned above, a chelating agent also participates in degrading the adsorbed polymer surface of the siliceous substrate. For example, at concentrations greater than about 500 μM of EDTA, there is a sharp reduction in the stability of the adsorbed polymer surface and delamination is apparent. It was observed that forced delamination occurs at greater than about 2 mM concentrations of ethylenediaminetetraacetic acid (EDTA). At about 2.5 mM concentrations of EDTA, the adsorbed polymer surface coating on a siliceous substrate will delaminate at a rate of about 50% to about 80%. Therefore, how much chelating agent to use in the hybridization solution will depend on many factors, which one skilled in the art can determine without undue experimentation using the information provided herein. The buffer composition comprises much less than 500 μM of a chelating agent, for example less than about 100 μM. Divalent cation chelating agents useful for the invention include, but are not limited to, EDTA, CDTA (trans-1,2-diaminocyclohexanetetraacetic acid) or DTPA (diethylenetriaminopentaacetic acid). The chelating agent EDTA is preferred for the buffer composition at a chelating agent concentration of less than about 100 μM, and preferably the chelating agent concentration is about 50 μM.

A surfactant is useful for providing better mixing of the hybridization solution, target material and the probes on the microarray. Moreover, higher concentrations of surfactants are useful when using hybridization buffer solutions in large volume hybridization chambers to facilitate the movement of bubbles formed in the hybridization chamber during the heating process. The buffer composition optionally further comprises a minimum amount of an ionic surfactant sufficient to facilitate bubble movement and to avoid developing unhybridized areas. The minimum amount of ionic surfactant is an amount sufficient to wet the surfaces of the hybridization chamber and loosen bubbles impinged on the surfaces of the hybridization chamber. Unless indicated otherwise, the term 'hybridization chamber' includes both large volume hybridization chambers and glass slide/cover slip hybridizations. In one embodiment, the concentration of ionic surfactant in the buffer composition ranges from about 0.01% to about 0.2% (w/v), and preferably ranges from about 0.02% to about 0.1% (w/v), with a concentration of less than or equal to about 0.10% (w/v) being recommended.

Moreover, increasing the amount of surfactant and/or the use of some surfactants will have a negative effect on the stability of an adsorbed polymer coated glass slide, in particular, a polycationic polymer coating. For example, the ionic surfactants, such as alkyl sulfate-containing surfactants, like sodium dodecyl sulfate (SDS), lithium lauryl sulfate (LLS), and N-lauryl sarcoside; amine-containing surfactants like acylated polypeptides, alkanolamine condensates, and N-alkylpyrrolidones; and sulfonate-containing surfactants like linear alkybenzene sulfonates, lignin sulfonates, paraffin sulfonates, sulfosuccinate esters, alkylnaphthalene sulfonates, isethionates, are all ionic surfactants that may be used in the invention. This invention also includes within its scope the use of other sulfonate or amine containing surfactants, such as sarcosinate-derived surfactants, and others not mentioned herein. However, Triton X-100® and X-102® are non-ionic octylphenoxy-polyoxyethylene ethers that are trademarks of Union Carbide. Certain surfactants, including Triton X-100® and X-102®, in low concentrations have a large negative effect on the stability of the adsorbed polymer surface for reasons that are not known. Further, the recommended surfactants, such as lithium lauryl sulfate (LLS), (a.k.a, LDS), sodium dodecyl sulfate (SDS), other aryl or alkyl sulfonate surfactants, used at concentrations above about 0.10% in the hybridization solution will have a negative effect on the stability of the adsorbed polymer surface, in particular, on a polycationic polymer surface. Therefore, how much and which surfactant to use in the buffer composition will depend on many factors, which one skilled in the art can determine without undue experimentation using the information provided herein.

A preferred buffer composition comprises a concentration of less than or equal to about 0.10% (w/v) sodium dodecyl sulfate (SDS) or lithium lauryl sulfate (LLS) surfactant in the buffer composition as a useful component to reduce the amount of degradation of nucleic acid targets during hybridization. The lithium salt in LLS has the advantage of being more soluble so the buffer preparation time is reduced. Further, a concentration that is less than or equal to about 0.1% (w/v) of SDS and LLS surfactants does not appear to have deleterious effects on an adsorbed polymer surface under most conditions. The hybridization solution of the invention was developed to use the minimum amount of surfactant to facilitate bubble movement and to avoid unhybridized areas in both large volume hybridization chambers and relatively smaller cover slip hybridization chambers.

In another aspect of the present invention, a method of hybridizing a microarray of oligonucleotides bound to an adsorbed polymer surface of a siliceous substrate with a nucleic acid material is provided. The method of hybridizing comprises the step incubating the nucleic acid material with the microarray of oligonucleotides on the adsorbed polymer surface in a hybridization solution at a hybridization temperature ranging from about 55° C. to about 70° C. so as to hybridize the nucleic acid material. The hybridization solution comprises a buffer composition that comprises a pH within a range of pH 6.4 to 7.5, a non-chelating buffering agent that maintains the pH within the pH range, and a monovalent cation that has a monovalent cation concentration ranging from about 0.01 M to about 2.0 M. Moreover, the buffer composition has a total cation concentration that ranges from about 0.02 M to about 2.0 M. In one embodiment, the method may further comprise the step of combining the nucleic acid material with the hybridization solution before the step of incubating with the microarray.

The hybridization solution used in the method has the buffer composition and any of its preferred embodiments that are described above. The hybridization temperature used in the present method preferably ranges from about 60° C. to 66° C. and is controlled in a temperature controlled water bath. Also the present method works particularly well on adsorbed polymer surfaces that comprise a polycationic polymer and where the oligonucleotides are cDNA.

The preferred polycationic polymer includes, but is not limited to, one or more of polyethylenediamine, polyacrylamide, poly-L-arginine, poly-L-histidine, and poly-L-lysine. All polycationic polymers that are or may be used to facilitate bonding or immobilization of nucleic acids or other biological materials to a microarray substrate surface are within the scope of the present invention.

The present buffer composition and method are useful for hybridization time periods ranging from less than about 2 hours to at least 48 hours. More importantly, the present invention works well where the conventional hybridization parameters fail (i.e., at the hybridization time of about 6 hours and much longer). The present invention works particularly well for hybridizations preferably taking up to at least about 24 hours, and more preferably between about 12 hours and about 24 hours. Advantageously, the present buffer composition and method overcome the problems of degraded adsorbed polymer surfaces during hybridizations at higher temperatures and for longer incubation time periods. Further advantageously, the buffer composition and method are applicable to both hybridizations in large volume chambers and relatively small volume cover slip hybridizations.

At the lower limit of pH 6.4 and below, more non-Watson/Crick base pairing (specifically A::C base-pairing) tends to occur. In accordance with the invention, non-Watson/Crick base pairing is acceptable, but not preferred. Further, below pH 6.4, unacceptable destruction of the adsorbed polymer surface coating occurs. Therefore, the lower limit of the pH range is not less than pH 6.4, and preferably, the lower limit is about pH 6.6, to reduce non-Watson/Crick base pairing and the adsorbed polymer surface destruction. Above the upper limit of the pH 7.5, the amount of observable hybridizations decreases, believed to be due to an increase in the adsorbed polymer surface degradation. Preferably, the upper limit in pH range is not more than pH 7.0, and more preferably pH 6.8, to further increase the amount of observable hybridizations at high temperatures. The pH range within pH 6.6 to 6.8 is more preferable, since the best hybridization and stability was observed in this pH range, with a pH of 6.7 being optimal. The more preferred embodiments of the present invention provides optimized hybridization results at conventionally high hybridization temperatures and long incubation time periods on adsorbed polymer surfaces of siliceous substrates.

In the present invention, generally the nucleic acid bound to the microarray surface may be either a probe or a target under test. Further, the other nucleic acid material may be either the probe or the target. However, when the probe is bound to the microarray, the other material is the target and where the target is bound to the microarray, the other material is the probe. Preferably, the nucleic acid bound to the surface is a probe of an oligonucleotide, more preferably, cDNA. The adsorbed polymer on the unused portions of the microarray surface may need to be capped or deactivated when all probes are attached and the microarray fabrication is completed, before exposure to the target material, according to conventional methods. Further, the target material or the probes may be directly or indirectly labeled using conventional methods, such that after hybridization, the targets or probes that are hybridized emit a signal when optically interrogated.

The resulting hybridized microarray of the invention is washed to flush unhybridized material off the surface and then spun or blown dry using conventional methods. The dried microarray is optically scanned to measure the degree of hybridization using conventional scanning equipment and techniques. Where the target or probe is indirectly labeled, a post-hybridization stain, such as streptavidin covalently linked to a fluorophore or colloidal gold, is typically applied to the microarray after hybridization, but before final washing. The signal intensities and locations of the signals on the microarray provide much information about the target material.

In another aspect of the invention, a buffer kit for a hybridization assay is provided. In one embodiment, the buffer kit comprises the buffer composition of the present invention, or any of its preferred embodiments, as described above. In another embodiment, the buffer kit comprises a list of the chemical components for the buffer composition. In each case, the kit is for use in a hybridization assay with a siliceous array substrate having an adsorbed polymer surface. When a nucleic acid material under test is attached to the adsorbed polymer surface of the array substrate, the buffer composition further comprises nucleic acids in solution to hybridize to the nucleic acid material on the array. Otherwise, a microarray populated with nucleic acids attached to the adsorbed polymer surface of the siliceous substrate is available to an user with the kit to hybridized to a nucleic acid material under test. The kit may optionally further comprise the microarray, and/or a nucleic acid sample as a hybridization assay control.

Still further, the buffer kit may further comprise instructions for using the buffer composition in a hybridization assay comprising the method of the present invention, or any of its preferred embodiments, as described above. The instructions may optionally further or alternatively include instructions for assaying the nucleic acid material under test on the siliceous array substrate with the nucleic acids in solution included in the buffer composition, as described above.

The list of components and the buffer composition of the kit embodiments comprise a non-chelating buffering agent; a monovalent cation; a pH within a range of pH 6.4 to 7.5; and a total cation concentration ranging from about 0.02 M to about 2.0 M. The non-chelating buffering agent maintains the pH within the range of pH 6.4 and 7.5. The monovalent cation is provided in a monovalent cation concentration ranging from about 0.01 M to about 2.0 M. The list and the buffer composition optionally may further comprise one or more of about 0.01% to about 0.2% (w/v) of an ionic surfactant and less than about 100 $\mu$M concentration of a chelating agent that chelates or sequesters divalent cations. The non-chelating buffering agent is selected from a group consisting of alkyl sulfonic acid-containing and alkyl amine-containing buffering agents that maintains the pH within the range of pH 6.4 and 7.5, as further described above. The monovalent cation is selected from the group consisting of one or more of LiCl, KCl, and NaCl and preferably has a monovalent cation concentration that ranges from about 0.10 M to about 2.0 M. The optional ionic surfactant is selected from the group consisting of one or more of an alkyl sulfate-containing, a sulfonate-containing or an amine-containing ionic surfactants, as further described above, and preferably has a surfactant concentration of about 0.02% to about 0.1% (w/v). The optional chelating agent is selected from the group consisting of EDTA, CDTA and DTPA, and preferably has a chelating concentration of about 50 $\mu$M. Further, the adsorbed polymer surface on the array or microarray substrate preferably comprises a polycationic polymer.

When the user receives the kit of the present invention, the user or an agent thereof (including but not limited to, a parent or a subsidiary of the parent or of the user, a contractor, subcontractor, vendor, customer, or the like) will typically expose an oligonucleotide sample to the microarray in accordance with the instructions. The hybridized array is then interrogated following exposure. Interrogation is usually accomplished by a suitable scanner that can read the location and intensity of fluorescence at each feature of an array following exposure to a fluorescently labeled sample (such as a polynucleotide containing sample). For example, such a scanner may be similar to the DNA Microarray Scanner available from Agilent Technologies, Palo Alto, Calif. Results from the interrogation can be processed results, such as obtained by rejecting a reading for a feature which is below a predetermined threshold and/or forming conclusions based on the pattern read from the array (such as whether or not a particular target sequence may have been present). The hybridization assay may be performed in a first location, the interrogation may be performed in the first or a second location different from the first by a user or an agent thereof, and the results of the interrogation (processed or not) can be forwarded (such as by communication) to a third location remote from the first or second location, if desired, and received there for further use by the user or an agent thereof.

By "remote" location, it is meant that the first, second or third location is at least in a different building from the others, and may be at least one mile, ten miles, or at least one hundred miles apart. "Communicating" information references transmitting the data representing that information as electrical signals over a suitable communication channel (for example, a private or public network). "Forwarding" an item (including information) refers to any means of getting that item from one location to the next, whether by physically transporting that item or otherwise (where that is possible) and includes, at least in the case of data, physically transporting a medium carrying the data or communicating the data.

The present invention allows sensitive, selective detection of nucleic acid targets, while preserving the intactness of the adsorbed polymer surface of the siliceous substrate. The buffer composition, method and kit of the invention overcome the problems found in the art of performing assays with microarrays of nucleic acids bound to an adsorbed polymer on a siliceous substrates at the high hybridization temperatures of between about 55° C. and 70° C. for long incubation times, such as greater than about 6 hours.

EXAMPLE

The following Example in Table 2 illustrates a most preferred buffer composition having a pH in the range of between pH 6.6 and 6.8 that may be used in the method of hybridizing of the invention. Microarrays of cDNA were attached to adsorbed polymer siliceous substrates coated with a poly-L-lysine polycationic polymer to facilitate bonding of the cDNA to the surface. The microarrays were exposed to the Example buffer composition in Table 2 below at a high hybridization temperature of 65° C. for about 18 hours. Another set of microarray samples was similarly exposed to a conventional SSC buffer composition. Delamination of the surface adsorbed polymer was monitored. The mean delamination rate and standard deviations are in Table 3 below.

TABLE 2

Example Of A 2x Hybridization Solution Comprising The Buffer Composition In Accordance With A Most Preferred Embodiment Of The Invention:

| Final Concentration* | Component | Volume ($\mu$l) |
|---|---|---|
|  | Nuclease-free water | 4776 |
| 717 mM | 8.0 M LiCl | 824 |
| ~400 mM | 1.0 M Li-MES (pH 6.7) | 4000 |
| 100 $\mu$M | 5.0 mM EDTA | 200 |
| 0.20% (w/v) | 10% Lithium Lauryl Sulfate | 200 |
| Volume 2x (ml) |  | 10 |

*The Example reflects the final concentrations of the components in the 2X buffer solution and the 2X buffer solution was diluted prior to use in the hybridization.

The Example reflects the final concentrations of the components in the 2X buffer solution and the 2X buffer solution was diluted prior to use in the hybridization.

TABLE 3

Samples Showing Delamination Of Adsorbed Polymer Surface Using Example Hybridization Solution Compared To Conventional SSC Buffer In Percent

| Buffer | Mean | Standard Deviation | Sample Count |
|---|---|---|---|
| Preferred Buffer | 0.39 | 0.78 | 109 |
| Conventional SSC | 28.7 | 34.53 | 105 |

The Example herein is illustrative only and not intended to limit the scope of the invention. The components, the volumes and the final concentrations may each vary and still be within the scope of the invention.

Thus there has been described a buffer composition, a method and a kit for hybridizing oligonucleotides or polynucleotides on a siliceous substrate having an adsorbed polymer surface at high hybridization temperatures. It should be understood that the above-described embodiments and examples are merely illustrative of the some of the many specific embodiments that represent the principles of the present invention. Clearly, numerous other arrangements can be readily devised by those skilled in the art without departing from the scope of the present invention.

What is claimed is:

1. A method of hybridizing a microarray of oligonucleotides bound to a polymer adsorbed on a surface of a siliceous substrate with a nucleic acid material comprising the step of
   incubating the nucleic acid material with the microarray of oligonucleotides on the adsorbed polymer surface in a hybridization solution at a hybridization temperature ranging from about 55° C. to about 70° C. so as to hybridize the nucleic acid material,
   wherein the hybridization solution comprises a buffer composition that comprises a pH within a range of pH 6.4 to 7.5, a non-chelating buffering agent that maintains the pH within the pH range, and a monovalent cation in a monovalent cation concentration ranging from about 0.01 M to about 2.0 M.

2. The method of claim 1, wherein in the step of incubating, the non chelating buffering agent is selected from a group consisting of 2-[N-morpholino]ethanesulfonic acid (MES), 3-(N-Morpholine)propanesulfonic acid (MOPS), Piperazine-N,N'-bis(2-ethansulfonic acid (PIPES), Tris(hydroxymethyl)aminomethane hydrochloride (TRIS-HCl), Hydroxyethylpiperazine-N'-2-ethanesulfonic acid (HEPES), and N-Tris(hydroxymethyl)methylglycine (TRICINE).

3. The method of claim 1, wherein in the step of incubating, the monovalent cation is selected from a salt consisting of one or more of LiCl, NaCl and KCl and the monovalent cation concentration ranges from about 0.1 M to about 2.0 M.

4. The method of claim 1, wherein the adsorbed polymer surface comprises a polycationic polymer.

5. The method of claim 4, wherein the polycationic polymer is selected from a group consisting of one or more of polyethylenediamine, poly-acrylamide, poly-L-arginine, poly-L-histidine, and poly-L-lysine.

6. The method of claim 1, wherein in the step of incubating, the buffer composition further comprises a chelating agent selected from a group consisting of one or more of ethylenediaminetetraacetic acid (EDTA),trans-1, 2-diaminocyclohexanetetraacetic acid (CDTA) and diethylenetriaminopentaacetic acid (DTPA) that has a chelating agent concentration of less than about 100 $\mu$M.

7. The method of claim 1, wherein in the step of incubating, the buffer composition further comprises an ionic surfactant selected from a group consisting of one or more of sodium dodecyl sulfate (SDS), lithium lauryl sulfate (LLS), N-lauryl sarcoside, acylated polypeptides, linear alkybenzene sulfonates, lignin sulfonates, paraffin sulfonates, sulfosuccinate esters, alkylnaphthalene sulfonates, isethionates, alkanolamine condensates, and N-alkylpyrrolidones, and wherein the step of incubating comprises using a hybridization chamber, and the ionic surfactant is provided in an amount sufficient to wet surfaces of the hybridization chamber and loosen bubbles impinged on the surfaces of the hybridization chamber.

8. The method of claim 7, wherein the amount of ionic surfactant is a surfactant concentration ranging from about 0.01% to about 0.2% (w/v).

9. The method of claim 1, wherein the buffer composition has a total cation concentration of about 0.02 M to about 2.0 M.

10. The method of claim 1, wherein in the step of incubating, the non chelating buffering agent is 2-[N-morpholino]ethanesulfonic acid (MES), the monovalent cation is LiCl, the monovalent cation concentration is greater than or equal to 300 mM, the pH is within the range of pH 6.6 to 6.8.

11. The method of claim 10, wherein in the step of incubating, the buffer composition further comprises one or both of a chelating agent ethylenediaminetetraacetic acid EDTA having a chelating agent concentration of about 50 $\mu$M, and an ionic surfactant selected from sodium dodecyl sulfate (SDS), lithium lauryl sulfate (LLS) having a surfactant concentration that ranges from about 0.02% to about 0.1% (w/v), and the buffer composition has a total cation concentration of about 750 mM.

12. The method of claim 1, before the step of incubating, further comprising the step of combining the nucleic acid material with the buffer composition.

13. The method of claim 1, after the step of incubating, further comprising the step of interrogating the hybridized microarray at a first location, the first location being a physical location either where the incubation of the microarray is performed or another location separate from the microarray incubation location.

14. The method of claim 13, further comprising the step of transmitting data representing a result of the interrogation.

15. The method of claim 14, further comprising the step of receiving the transmitted data at a second location, the second location being a physical location that is different from one or both of the first location where the microarray interrogation is performed and the microarray incubation location.

16. The method of claim 15, wherein the first location is remote from the second location, the remote first location being physically separated from the second location.

17. A method of performing a high temperature hybridization assay comprising the step of:

incubating a nucleic acid material with a microarray of oligonucleotides in a hybridization solution at a hybridization temperature ranging from about 55° C. to about 70° C. so as to hybridize the nucleic acid material, wherein the microarray comprises a siliceous substrate with an adsorbed polymer surface and oligonucleotides bound to the adsorbed polymer surface, and wherein the hybridization solution comprises a pH within a range of pH 6.4 and 7.5 and a buffer composition, the buffer composition comprising a non-chelating buffering agent that maintains the pH within the range and a monovalent cation having a monovalent cation concentration ranging from 0.01 M and 2.0 M.

18. A method of hybridizing a microarray of oligonucleotides with a nucleic acid material comprising the step of:

incubating the nucleic acid material with the microarray of oligonucleotides in a hybridization solution at a hybridization temperature ranging from about 55° C. to about 70° C. so as to hybridize the nucleic acid material, the oligonucleotides being bound to a polymer coating adsorbed on a surface of a siliceous substrate, the adsorbed polymer coating being non-covalently bound to the siliceous substrate surface, wherein the hybridization solution comprises a buffer composition that comprises a pH within a range of pH 6.4 to 7.5, a non-chelating buffering agent that maintains the pH within the pH range, and a monovalent cation in a monovalent cation concentration ranging from about 0.01 M to about 2.0 M.

19. The method of claim 18, wherein the non chelating buffering agent is 2-[N-morpholino]ethanesulfonic acid (MES), the monovalent cation being LiCl, the monovalent cation concentration being greater than or equal to about 300 mM, the pH being within the range of about pH 6.6 to about 6.8, and wherein the adsorbed polymer coating is a polycationic polymer.

20. A method of reducing surface degradation to a microarray of oligonucleotides during a high temperature hybridization assay comprising:

incubating a nucleic acid material with the microarray of oligonucleotides in a hybridization solution at a hybridization temperature ranging from about 55° C. to about 70° C. so as to hybridize the nucleic acid material, the oligonucleotides being bound to a polycationic polymer that is adsorbed to a surface of a siliceous substrate, the adsorbed polycationic polymer being non-covalently bound to the siliceous substrate surface, wherein the hybridization solution comprises a buffer composition that comprises a pH within a range of pH 6.4 to 7.5, a non-chelating buffering agent that maintains the pH within the pH range, and a monovalent cation in a monovalent cation concentration ranging from about 0.01 M to about 2.0 M.

* * * * *